United States Patent
Phillips et al.

(10) Patent No.: US 9,470,620 B2
(45) Date of Patent: Oct. 18, 2016

(54) INSULATOR INSPECTION APPARATUS AND METHOD

(71) Applicant: ELECTRIC POWER RESEARCH INSTITUTE, INC., Charlotte, NC (US)

(72) Inventors: Andrew John Phillips, Harrisburg, NC (US); Timothy Scott Shaw, Charlotte, NC (US); Kristopher C. Kozak, San Antonio, TX (US); Jerry A. Towler, San Antonio, TX (US)

(73) Assignee: ELECTRIC POWER RESEARCH INSTITUTE, INC., Charlotte, NC (US)

( * ) Notice: Subject to any disclaimer, the term of this patent is extended or adjusted under 35 U.S.C. 154(b) by 486 days.

(21) Appl. No.: 14/017,874

(22) Filed: Sep. 4, 2013

(65) Prior Publication Data

US 2014/0074411 A1 Mar. 13, 2014

Related U.S. Application Data

(60) Provisional application No. 61/698,927, filed on Sep. 10, 2012.

(51) Int. Cl.

| | |
|---|---|
| *G01N 19/08* | (2006.01) |
| *G01N 3/30* | (2006.01) |
| *G01N 29/04* | (2006.01) |
| *G01N 29/14* | (2006.01) |
| *G01N 29/46* | (2006.01) |
| *G01R 31/12* | (2006.01) |

(52) U.S. Cl.
CPC .......... *G01N 19/08* (2013.01); *G01N 3/30* (2013.01); *G01N 29/045* (2013.01); *G01N 29/14* (2013.01); *G01N 29/46* (2013.01); *G01N 2203/0244* (2013.01); *G01N 2291/2697* (2013.01); *G01R 31/1209* (2013.01)

(58) Field of Classification Search
None
See application file for complete search history.

(56) References Cited

U.S. PATENT DOCUMENTS

| 4,869,175 A | * | 9/1989 | McDougal | ............ F41H 5/0428 |
| | | | | 102/501 |
| 7,278,290 B1 | * | 10/2007 | Hughes | .................... C09K 9/00 |
| | | | | 264/103 |
| 2007/0260407 A1 | * | 11/2007 | Van Albert | .......... A61B 5/6805 |
| | | | | 702/57 |
| 2010/0100239 A1 | * | 4/2010 | Park | .................. G01R 31/1245 |
| | | | | 700/258 |
| 2012/0188078 A1 | * | 7/2012 | Soles | ................... G08B 13/126 |
| | | | | 340/540 |
| 2013/0174639 A1 | * | 7/2013 | Earthman | ................ A61B 9/00 |
| | | | | 73/12.01 |

OTHER PUBLICATIONS

Colon, Hector, Adam Horton, Kyle Steighner, and Nicholas Yielding. Autonomous Turret. EE4914 Group 17, University of Central Florida, 2010.*

(Continued)

*Primary Examiner* — Aditya Bhat
(74) *Attorney, Agent, or Firm* — Trego, Hines & Ladenheim, PLLC; Brandon Trego; Jonathan Hines

(57) ABSTRACT

An insulator inspection tool and method for identifying defects or conditions that may prevent the insulator from performing properly is disclosed. The apparatus includes a launcher adapted to launch a projectile towards an insulator being tested, a listening device adapted to receive a response signal from the insulator upon being struck by the projectile, and a processing device adapted to measure the response signal received by the listening device and process the response signal to determine whether the insulator contains any defects or conditions.

15 Claims, 7 Drawing Sheets

(56) References Cited

OTHER PUBLICATIONS

Prosser, William, Madaras, Eric, Studor, George, Gorman, Michael, "Acoustic Emission Detection of Impact Damage on Space Shutttle Structures" NASA Langley Research Center. Feb. 2004.*

Model Pulse M74DP Dual power Mini Airsoft Machine Gun wner's Manual, Obtained from Wayback machine Sep. 26, 2010.*

Carne, T.G. & Stasiunas, E.C. Lessons Learned in Modal Testing—Part 3: Transient Excitation for Modal Testing, More than Just Hammer Impacts. Society for Experimental Mechanics. May/Jun. 2006.*

Proceedings of the 5th International Conference on Properties and Applications of Dielectric Materials, 1997, 766-769 vol. 2, Seoul, Korea.

CIAP: Cracked Insulator Acoustic Probe, Hydro Quebec, Product Catalog Mar. 2010, www.technerds.ca, Canada.

* cited by examiner

INSULATOR INSPECTION APPARATUS AND METHOD

BACKGROUND OF THE INVENTION

This application relates to an insulator inspection tool and method. More particularly, it relates to a porcelain insulator inspection tool and method for identifying defects or conditions that may prevent the insulator from performing properly.

Porcelain Insulators are widely used in electrical distribution systems. One area in particular where porcelain insulators are used is in substations and on overhead electrical transmission lines. These insulators help support transmission lines and insulate supports, such as wood poles, from arcing or leakage of electricity.

Unfortunately, porcelain insulators may have or may develop defects and conditions in the porcelain which prevent the insulators from performing properly (mechanically or electrically), or be an indicator of a defect or condition that with time may result in the insulator being unable to perform at all. In particular, the defects or conditions of interest are internal cracking (FIG. 2) or external cracking which is visible upon close inspection (FIG. 1). For external cracks, it is common for utility personnel to either use close-up visual techniques or strike the insulator with a hard (metal) object and listen to the tone of the porcelain's response. This creates safety issues with in-service, energized transmission lines.

Accordingly, there is a need for an inspection apparatus that allows utility personnel to safely inspect insulators deployed in energized distribution systems.

BRIEF SUMMARY OF THE INVENTION

These and other shortcomings of the prior art are addressed by the present invention, which provides an insulator inspection apparatus and method that provides a low cost technique that allows field personnel to remotely inspect porcelain insulators while in-service and under energized conditions.

According to one aspect of the invention, an apparatus adapted to identify defects or conditions in an insulator deployed in an energized electrical distribution system includes a launcher adapted to launch a projectile towards an insulator being tested, a listening device adapted to receive a response signal from the insulator upon being struck by the projectile, and a processing device adapted to measure the response signal received by the listening device and process the response signal to determine whether the insulator contains any defects or conditions.

According to another aspect of the invention, an apparatus adapted to identify defects in a porcelain insulator deployed in an energized electrical distribution system includes a launcher having a tube adapted to receive a projectile therein and to allow a user to accurately aim the launcher at the insulator, and a trigger operably connected to the tube, wherein activation of the trigger causes the projectile to be propelled down the tube towards the insulator. The apparatus further includes a listening device adapted to receive a response signal from the insulator upon being struck by the projectile, and a processing device adapted to measure the response signal received by the listening device and process the response signal to determine whether the insulator contains any defects.

According to another aspect of the invention, a method of determining a condition of an insulator deployed in an energized electrical distribution system includes the steps of providing an apparatus having a launcher, a listening device, and a processing device. The method further includes the steps of using the launcher to propel a projectile towards an insulator to be tested and thereby strike the insulator with the projectile, using the listening device to capture a resonate response signal from the insulator; and using the processing device to measure and process the resonate response signal to determine whether the insulator contains any defects or conditions.

BRIEF DESCRIPTION OF THE DRAWINGS

The subject matter that is regarded as the invention may be best understood by reference to the following description taken in conjunction with the accompanying drawing figures in which.

DETAILED DESCRIPTION OF THE INVENTION

Figure 1:
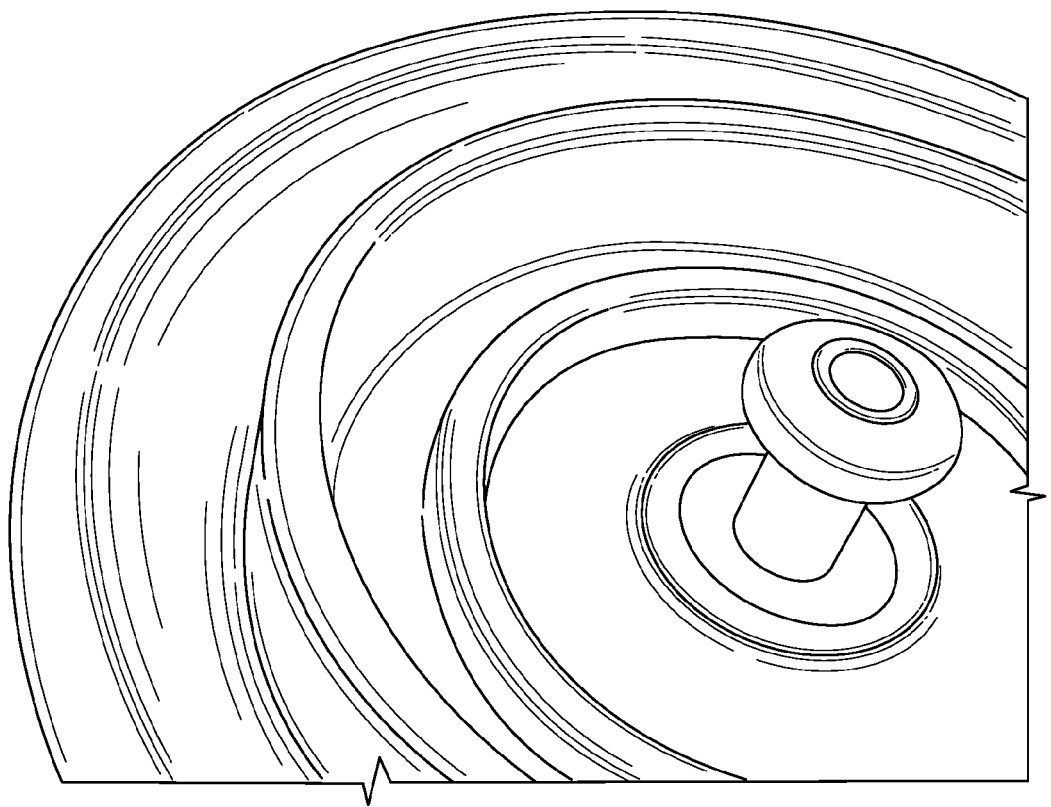
FIG. 1 shows an insulator with an external crack.
Figure 2:
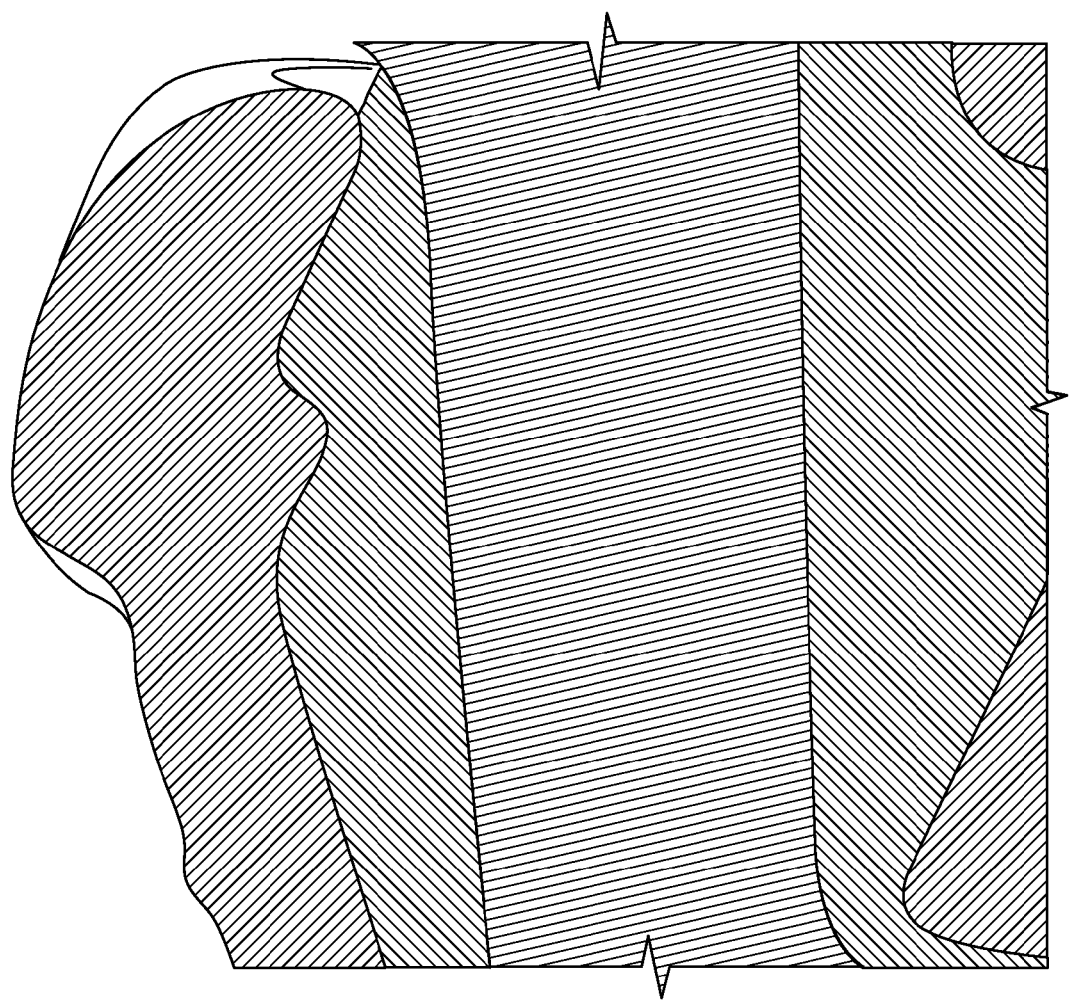
FIG. 2 shows an internal crack of an insulator.
Figure 3:
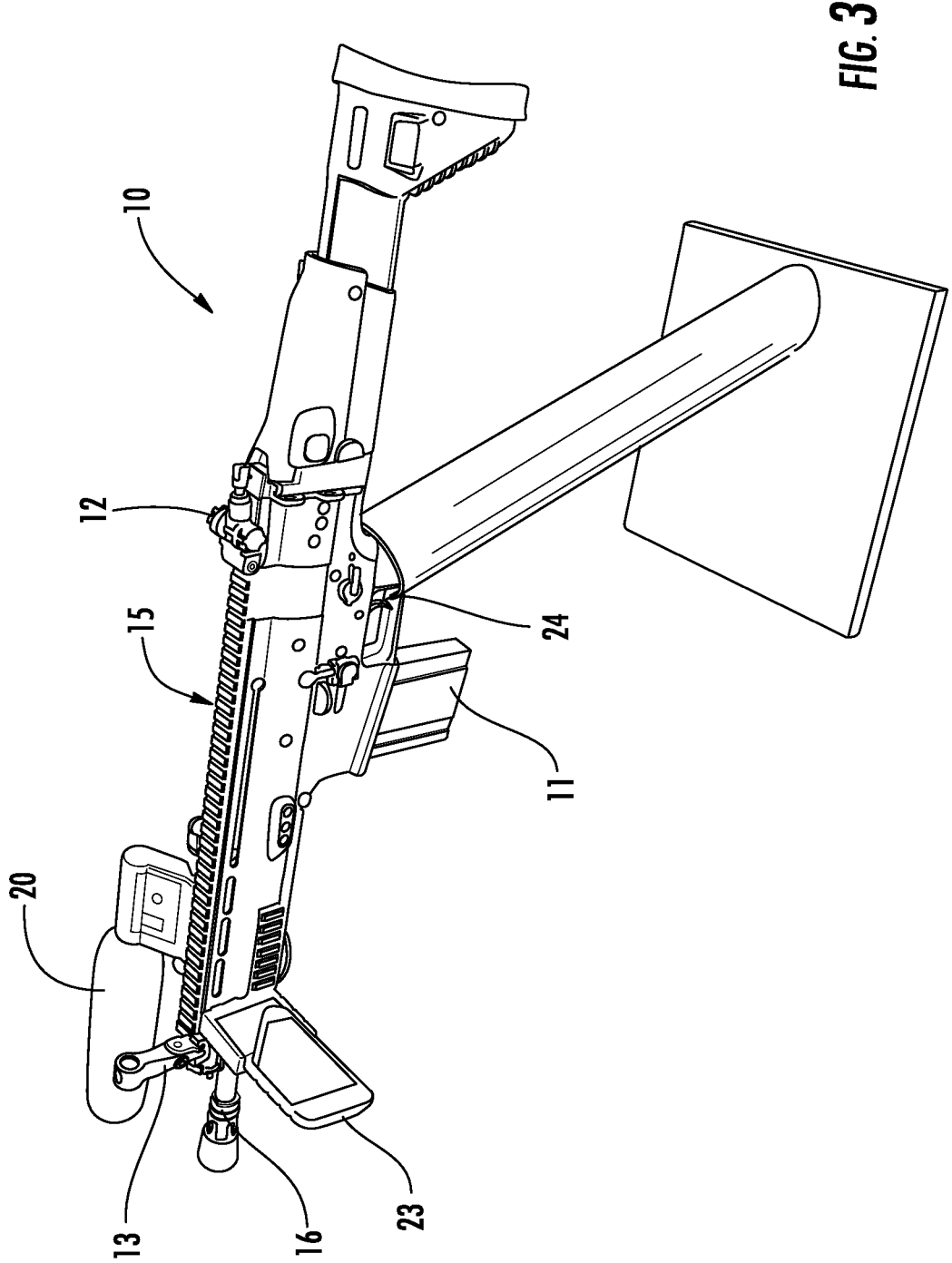
FIG. 3 shows an apparatus for inspecting an insulator according to an embodiment of the invention.
Figure 4:
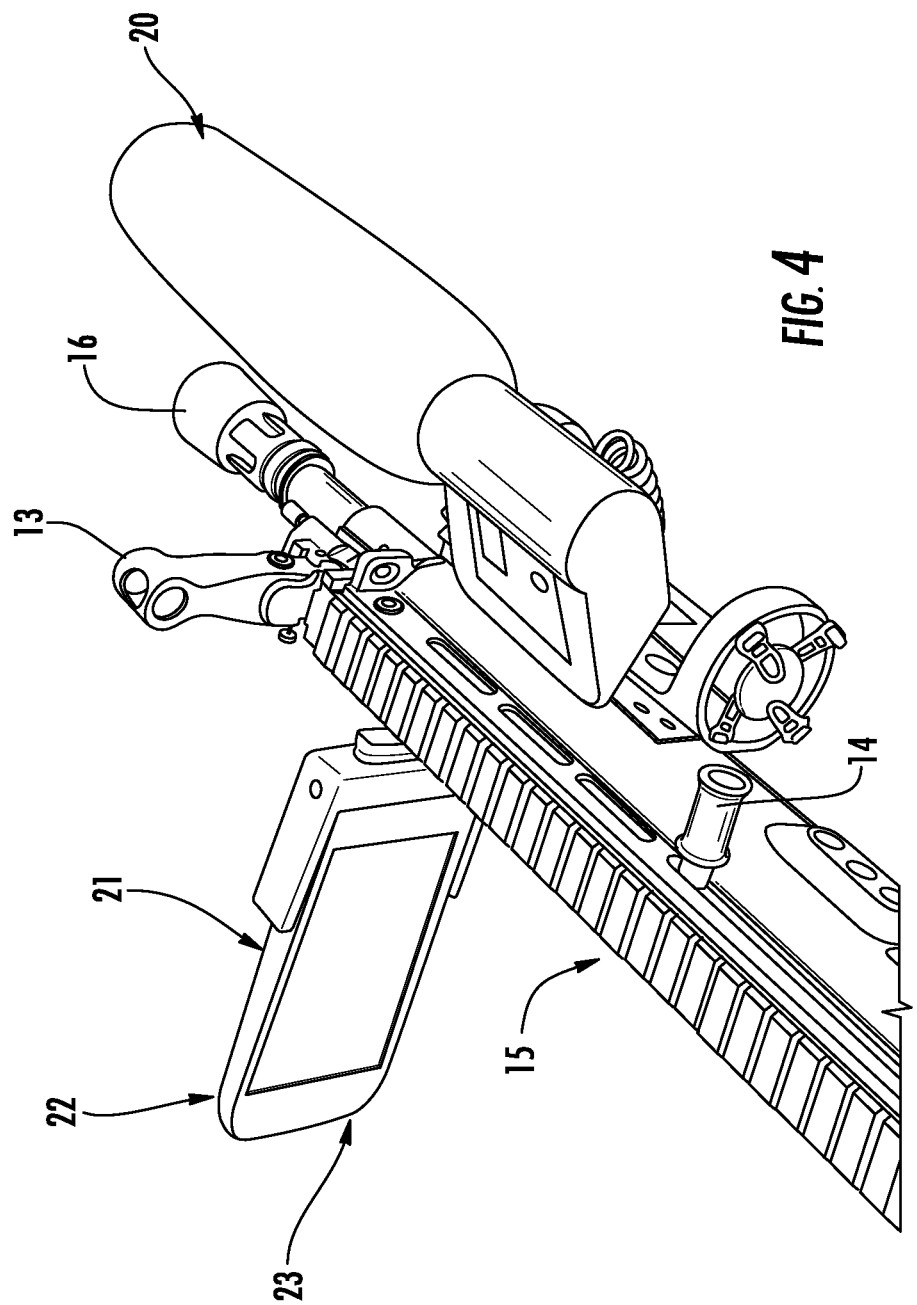
FIG. 4 shows inspection components of the apparatus of FIG. 3.

Referring to the drawings, an exemplary insulator inspection apparatus according to an embodiment of the invention is illustrated in FIGS. 3 and 4 and shown generally at reference numeral 10. The apparatus 10 is designed to shoot, propel, or launch a plastic projectile at a porcelain insulator. As shown, the apparatus 10 includes a launcher 15 in the form of a firearm to allow a user to easily target and fire a plastic projectile at an insulator. As shown, the launcher 15 includes a magazine 11 for containing plastic projectiles, a rear sight 12 and a front sight 13 to allow a user to aim the launcher 15, and an action 14 for loading a projectile from the magazine 11 into a barrel 16 mated to the action 14 and launching the projectile down the barrel 16 towards the insulator. While the launcher 15 is being discussed in reference to a firearm form, it should be appreciated that the firearm form is just one type of launcher and that other suitable launching-type systems that launch a plastic projectile accurately may be used.

As shown in FIG. 4, the apparatus 10 also includes a microphone 20, a Global Positioning System (GPS) 21 to allow a user to record the location of the insulator being tested, a camera 22 to allow a user to photograph the insulator being tested, and a smartphone 23 connected to the microphone 20 and loaded with an application for measuring and processing a response from the insulator.

In use, a user loads the magazine 11 of the launcher 15 with a plastic projectile by moving the action 14 from a fire position to a load position. Once a projectile has been removed from the magazine 11, the action 14 is released into the fire position. The user then aims the apparatus 10 at an insulator and launches the projectile at the desired insulator by depressing or activating a trigger 24. As used herein, a trigger refers to any device that initiates the process of propelling the projectile towards the insulator. It should be appreciated that while these steps are being detailed for a launcher in a firearm form, much simpler steps may be used for other suitable launchers, such as a tube connected to a compressed air supply.

Figure 5:
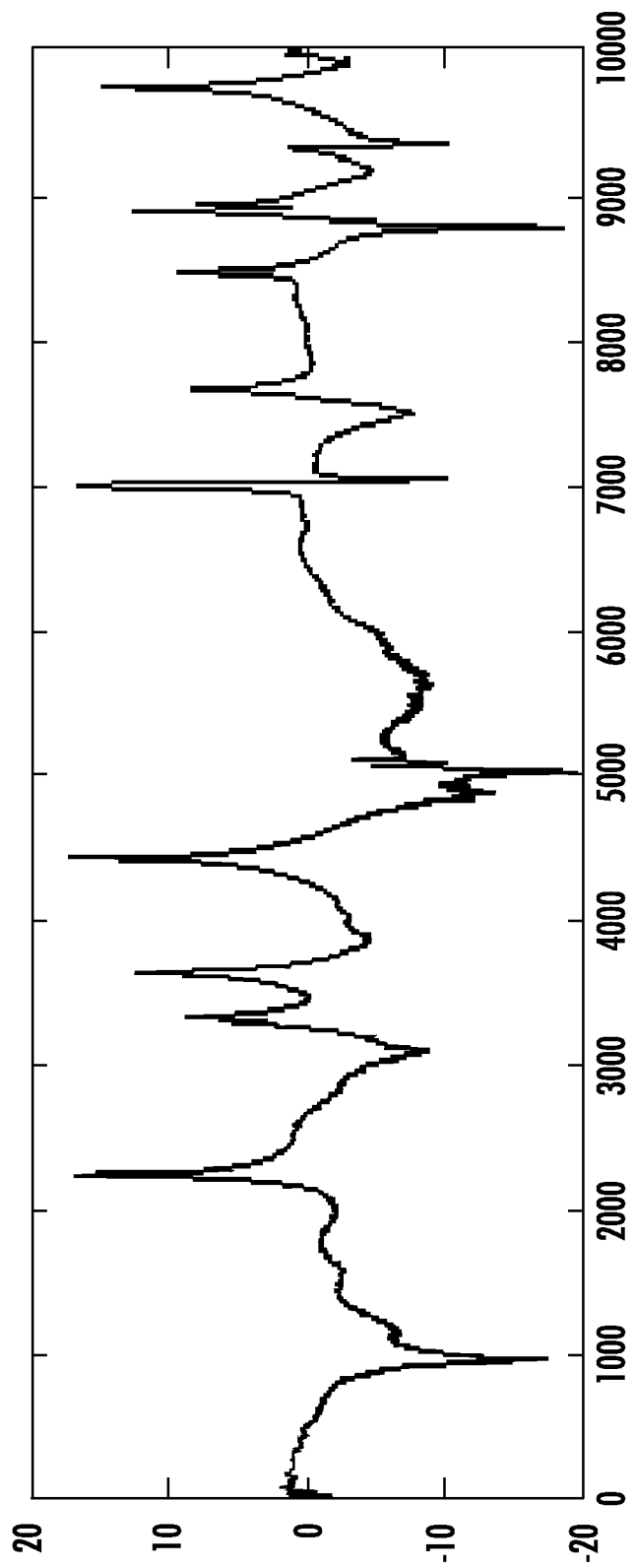
FIG. 5 shows a Fast Fourier Transform of a measured response from an insulator tested with the apparatus of FIG. 3.
Figure 6:
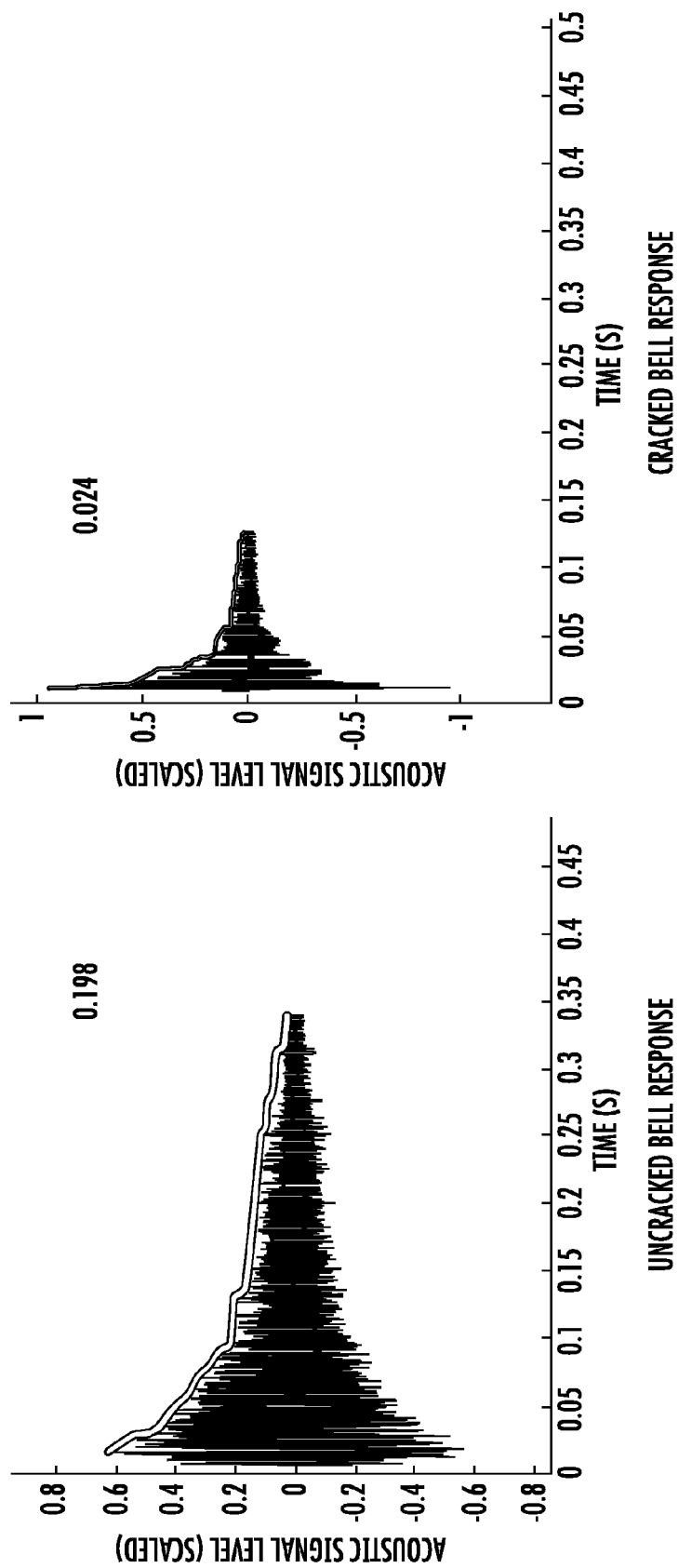
FIG. 6 provides a comparison of decay times of cracked and uncracked insulators.

Once the trigger 24 is depressed, the projectile is launched through the barrel 16 and strikes the insulator. The projectile may be launched using compressed air, a propellant, or any other suitable method. The strike by the projectile on the insulator causes the porcelain to resonate. The resonate response is captured by microphone 20 and sent to smartphone 23 where the resonate signal is digitized and measured. The application on the smartphone processes the measured response and determines the insulators condition based on one of two methods: (1) Fast Fourier transform (FFT) which determines the frequency components of the resonate signal (FIG. 5) and (2) the decay time of the measured response (FIG. 6). As shown in FIG. 6, a comparison of the decay times allow a user to determine the condition of the insulator. It should be understood that pre-determined responses for different types of insulators may be developed in a lab for comparison in the field.

Figure 7:
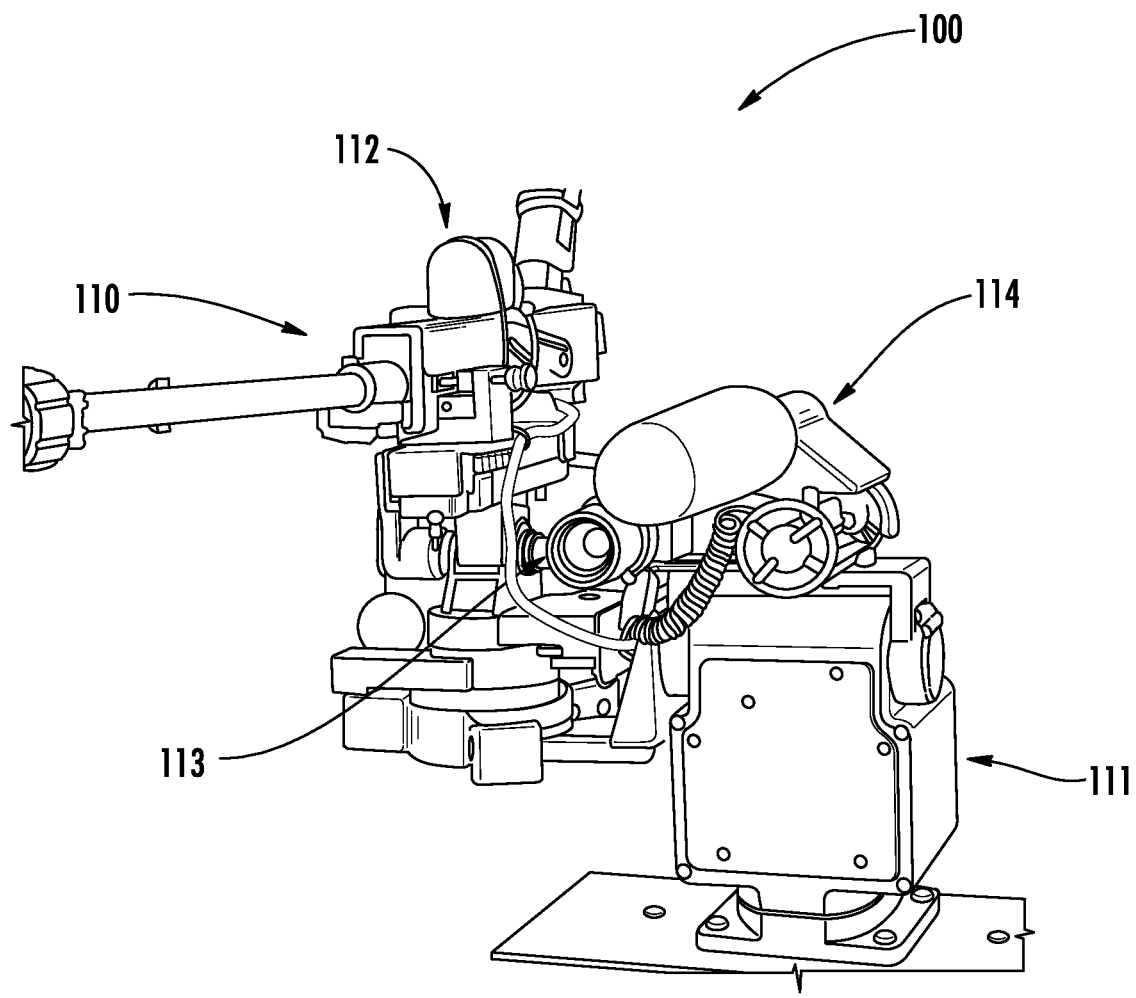
FIG. 7 shows an apparatus for inspecting an insulator according to an embodiment of the invention.

Referring to FIG. 7, an apparatus 100 according to an embodiment of the invention is shown. The apparatus 100 includes a launcher, such as an airsoft rifle 110 mounted to a 3D pan and tilt system 111 which is controlled by a computer (not shown). A camera 112 is mounted to the rifle 110 to aim the rifle 110 via a computer interface. The apparatus 100 further includes a high speed camera 113 connected to the computer to track pellet trajectory, a separate microphone 114 to receive resonate signals from the insulator being tested, an analog to digital converter (not shown) to digitize a measured response to the computer, and computer software to perform an analysis of the measure response. The apparatus 100 operates in much the same way as the apparatus 10. In particular, the apparatus 100 shoots a projectile at an insulator to be tested and records the response.

The foregoing has described an insulator inspection apparatus and method. While specific embodiments of the present invention have been described, it will be apparent to those skilled in the art that various modifications thereto can be made without departing from the spirit and scope of the invention. Accordingly, the foregoing description of the preferred embodiment of the invention and the best mode for practicing the invention are provided for the purpose of illustration only and not for the purpose of limitation.

We claim:

1. An apparatus adapted to identify defects or conditions in an electrical insulator deployed in an energized electrical distribution system, comprising:
    (a) a launcher adapted to launch a projectile towards an electrical insulator deployed in an energized electrical distribution system, wherein the launcher is located at a suitable distance from the electrical insulator to ensure a user's safety from the energized electrical distribution system;
    (b) a microphone co-located with the launcher and adapted to receive a response signal from the electrical insulator upon being struck by the projectile; and
    (c) a processing device operably connected to the microphone and programmed to determine whether or not the electrical insulator is defective based on the characteristics of the response signal.

2. The apparatus according to claim 1, wherein the launcher is in the form of a firearm to allow a user to accurately aim and launch the projectile towards the insulator.

3. The apparatus according to claim 1, further including a 3D pan and tilt system to aim the launcher via a computer interface.

4. The apparatus according to claim 1, further including a Global Positioning System (GPS) to allow a user to record the location of the insulator being tested.

5. The apparatus according to claim 1, further including a camera to allow a user to take photographs of the insulator being tested.

6. The apparatus according to claim 5, wherein the camera is a high speed camera to allow a user to track a trajectory of the projectile as it is propelled towards the insulator.

7. An apparatus adapted to identify defects in a porcelain insulator deployed in an energized electrical distribution system, comprising:
    (a) a launcher configured to propel a plastic projectile from a location remote from the porcelain insulator such that the remote location provides a user with a separation from the energized electrical distribution system, the launcher having:
        (i) a tube adapted to receive the plastic projectile therein and to allow a user to accurately aim the launcher at the insulator; and
        (ii) a trigger operably connected to the tube, wherein activation of the trigger causes the plastic projectile to be propelled down the tube towards the insulator, such that impact of the plastic projectile with the insulator causes the insulator to resonate without damaging the insulator to provide a response signal;
    (b) a microphone co-located with the launcher at the remote location and adapted to receive the response signal from the insulator upon being struck by the plastic projectile; and
    (c) a processing device operably connected to the microphone and programmed to measure the response signal received by the microphone and determine whether the insulator contains any defects.

8. The apparatus according to claim 7, wherein the processing device is a smartphone loaded with an application for measuring and processing the response from the insulator.

9. The apparatus according to claim 7, wherein the processing device digitizes the response signal and determines the insulator's condition by using Fast Fourier Transform (FFT) to determine frequency components of the response signal.

10. The apparatus according to claim 7, wherein the processing device digitizes the response signal and determines the insulator's condition by analyzing a decay time of the response signal and comparing the decay time to known decay times for insulators.

11. A method of determining a condition of an electrical insulator deployed in an energized electrical distribution system from a remote location, comprising the steps of:
    (a) providing an apparatus having:
        (i) a launcher;
        (ii) a microphone co-located with the launcher; and
        (iii) a processing device operably connected to the microphone;
    (b) positioning the apparatus at a location remote from an electrical insulator deployed in an energized electrical distribution system such that the remote location allows a user of the apparatus to remain a safe distance from the energized electrical distribution system;

(b) using the launcher to propel a projectile towards the electrical insulator to be tested, thereby striking the insulator with the projectile to cause the electrical insulator to resonant without damaging the electrical insulator;

(c) using the microphone to capture a resonate response signal from the electrical insulator upon being struck by the projectile; and (d) using the processing device to measure and process the resonate response signal to determine whether the insulator contains any defects or conditions.

12. The method according to claim 11, further including the step of loading a projectile into the launcher.

13. The method according to claim 11, further including the step of activating a trigger of the launcher to propel the projectile.

14. The method according to claim 11, wherein the step of using the processing device further includes the step of utilizing Fast Fourier Transform (FFT) to determine frequency components of the resonate response signal.

15. The method according to claim 11, wherein the step of using the processing device further includes the step of analyzing a decay time of the resonate response signal and comparing the decay time to known decay times for insulators.

* * * * *